United States Patent [19]

Imparato

[11] Patent Number: 5,045,069
[45] Date of Patent: Sep. 3, 1991

[54] PORTABLE INFUSION MONITOR

[76] Inventor: Robert Imparato, 17 Rolling Wood Dr., Trumbull, Conn. 06611

[21] Appl. No.: 297,652

[22] Filed: Jan. 17, 1989

[51] Int. Cl.$^5$ .............................................. A61M 5/00
[52] U.S. Cl. .................................. 604/253; 604/251; 73/861.41; 128/DIG. 13
[58] Field of Search ............... 604/253, 255, 250, 251, 604/246, 65, 67; 128/DIG. 13; 73/861, 861.41

[56] References Cited

U.S. PATENT DOCUMENTS

| | | | |
|---|---|---|---|
| 3,563,090 | 2/1971 | Deltour | 604/253 |
| 4,018,362 | 4/1977 | Ubaud | 222/55 |
| 4,038,982 | 8/1977 | Burke et al. | 128/214 E |
| 4,137,940 | 2/1979 | Faisandier | 604/253 |
| 4,173,224 | 11/1979 | Marx et al. | 128/214 E |
| 4,261,388 | 4/1981 | Shelton | 137/486 |
| 4,286,590 | 9/1981 | Murase | 604/253 |
| 4,346,606 | 8/1982 | Cannon et al. | 73/861.41 |
| 4,397,648 | 8/1983 | Knute | 604/253 |
| 4,432,761 | 2/1984 | Dawe | 604/253 |
| 4,509,943 | 4/1985 | Hanzawa | 604/31 |
| 4,551,134 | 11/1985 | Slavik et al. | 604/67 |
| 4,576,592 | 3/1986 | Danby | 604/253 |
| 4,668,216 | 5/1987 | Martin et al. | 604/296 |
| 4,681,563 | 7/1987 | Deckert et al. | 604/67 |
| 4,681,569 | 7/1987 | Coble et al. | 604/253 |
| 4,718,896 | 1/1987 | Arndt et al. | 73/861.4 |
| 4,722,734 | 2/1988 | Kolln | 604/151 |
| 4,781,698 | 11/1988 | Parren | 604/251 |

FOREIGN PATENT DOCUMENTS 875766  7/1971  Canada ............................... 604/253

Primary Examiner—C. Fred Rosenbaum
Assistant Examiner—Kathleen A. Daley
Attorney, Agent, or Firm—John R. Doherty

[57] ABSTRACT

A portable, self contained, infusion monitor is disclosed which can be easily and quickly attached to the drip chamber of an IV set. The monitor detects each drop of liquid falling through the drip chamber and calculates the volumetric flow rate of liquid passing through the IV set. A display for visually recording the flow rate is provided on the monitor along with an adjustable control member for calibrating the monitor for use with any IV set employing tubing having any drop factor.

12 Claims, 6 Drawing Sheets

| DROP FACTOR ||
|---|---|
| DROPS | VOLUME |
|  | (ML) |
| 10 | 1 |
| 15 | 1 |
| 20 | 1 |
| 30 | 1 |
| 60 | 1 |

PORTABLE INFUSION MONITOR

The present invention relates to intravenous infusion sets and more particularly to a portable infusion monitor for determining the volumetric flow rate of fluid passing through such intravenous infusion sets.

BACKGROUND OF THE INVENTION

Intravenous (IV) infusion sets are commonly employed to administer fluids containing medication and/or nutrients to both medical and surgical patients at a controlled rate. The rate may be controlled manually by adjusting a mechanical clamp on the IV tubing while counting drops falling through the drip chamber over a predetermined period of time to achieve a desired drop rate.

The amount of fluids to be administered to a patient is usually prescribed by the attending physician in cubic centimeters per hour, for example. It is necessary then for the operator to convert the drop rate into equivalent volumetric units. This is customarily done by dividing the drop rate by a number representing the so-called "drop factor" of the IV tubing. The drop factor varies with the size of the tubing and is expressed as a whole number, e.g., 10, 15, 20, 30, etc., marked on the package for the IV tubing, for example. Thus, in a particular case where the IV tubing has a drop factor of "10", for example, each volumetric unit, e.g. milliliter (ml), will produce 10 drops of liquid falling through the drip chamber.

While IV sets which are manually controlled in the aforesaid manner are quite simple and inexpensive to use, they are nonetheless time consuming and require experience and an ability to perform mathematical calculations in order to operate with any degree of accuracy.

Control devices for automatically regulating the flow rate of fluids in intravenous infusion sets have been developed such as those disclosed, for example, in U.S. Pat. Nos. 4,038,982 and 4,261,388. These devices generally include a valve for controlling the flow of fluid through the IV tubing and an electronic circuit for controlling the valve in order to establish a desired flow rate. A drop detector is usually also employed for sensing drops of liquid falling through the drip chamber.

Although control devices of this type are an improvement over prior manual techniques, they are nevertheless expensive and complex and generally require specially trained operators for their use. Moreover, most of these control devices are not capable of measuring the drop volume and also must be used with specific IV sets supplied with the device.

U.S. Pat. No. 4,173,224 to Marx et al. discloses an automatic IV regulator which employs an optical system for measuring the drop volume, but this system, while a distinct improvement, greatly increases the cost and complexity of the device.

It is therefore an important object of the present invention to provide a device for monitoring the volumetric flow rate of an infusion liquid flowing through an IV set which is inexpensive and which is easy to use.

Another object of the invention is to provide such a monitoring device which is portable and which can be used universally with any IV set employing tubing having any drop factor.

A more specific object of the invention is to provide a portable, self-contained, infusion monitor which can be easily attached to the drip chamber of one IV set and then quickly detached for use in another IV set without disturbing operation of either infusion system.

Another specific object is to provide such a portable, self-contained, infusion monitor which can be easily and quickly calibrated to accomodate IV sets employing tubing having varying drop factors.

Still another object is to provide such a portable, self-contained, infusion monitor which can visually display the volumetric flow rate of each drop of liquid falling through the drip chamber.

SUMMARY OF THE INVENTION

The present invention is directed to a device for monitoring the volumetric flow rate of an infusion liquid flowing through an IV set comprising, in combination:
a housing;
means for detachably mounting the housing onto a drip chamber forming part of the IV set; means for detecting each drop of liquid falling through the drip chamber;
means for measuring the time interval between successive drops of liquid;
means responsive to the measured time interval for determining the rate at which the drops fall through the drip chamber and for producing a signal representing the drop rate
means for generating an input signal representing the drop volume;
means coupled to the drop rate determining means and the input signal generating means for combining the two signals and producing an output signal representing the volumetric flow rat of liquid passing through the IV set; and
means for visually displaying the output signal.

In a preferred embodiment of a monitoring device according to the invention, the housing includes a surface portion which is adapted to contact one side of the drip chamber. The detachable mounting means includes a movable contact member and a biasing means for urging the movable contact member into contact with an opposite side of the drip chamber.

The drop detecting means used in the preferred device includes a photoelectric cell and a light source for passing a beam of light through the drip chamber in the direction of the photoelectric cell. The photoelectric cell may be mounted within the surface portion of the housing adapted to contact the drip chamber and the light source may be mounted within the movable contact member, for example.

The time interval measuring means comprises a clock and a pulse counter coupled to the drop detector for counting the number of pulses produced between successive drops of liquid falling through the drip chamber. A pair of pulse counters connected in parallel may also be employed to count the pulses produced between alternate drops of liquid.

The drop rate determining means used in the preferred device includes a first divider having an input connected to the time interval measuring means for calculating the rate at which each drop falls through the drip chamber. A multiplier having an input connected to the first divider is further provided for converting the drop rate to a higher order of time, e.g., drops/minute to drops/hour, for example.

The input signal generating means includes a variable potentiometer and means external to the housing for manually setting the potentiometer. Such external means may include, for example, a sliding control member and scale with markings indicating appropriate drop factor values.

The output signal producing means may include a second divider having a first input connected to the multiplier and a second input connected the potentiometer for operatively converting the drop rate to a volumetric flow rate.

The display means may be provided in the form of a liquid crystal mounted onto an exterior portion of the housing. The liquid crystal is operatively connected to the second divider for visually displaying the volumetric flow rate.

The monitoring device of the present invention is portable and self-contained and can be easily and quickly attached to a given intravenous (IV) set for determining the volumetric flow rate of the infusion liquid and then just as easily and quickly detached for use with another IV set without disturbing operation of the infusion systems. Moreover, the monitoring device is simple in construction and operation and is easy to use and economical to manufacture.

BRIEF DESCRIPTION OF THE DRAWING

The present invention, together with the foregoing and other objects and attendant advantages, will best be understood by reference to the following detailed description of a preferred embodiment thereof taken in conjunction with the accompanying drawing, wherein.

DESCRIPTION OF THE PREFERRED EMBODIMENTS

Figure 1:
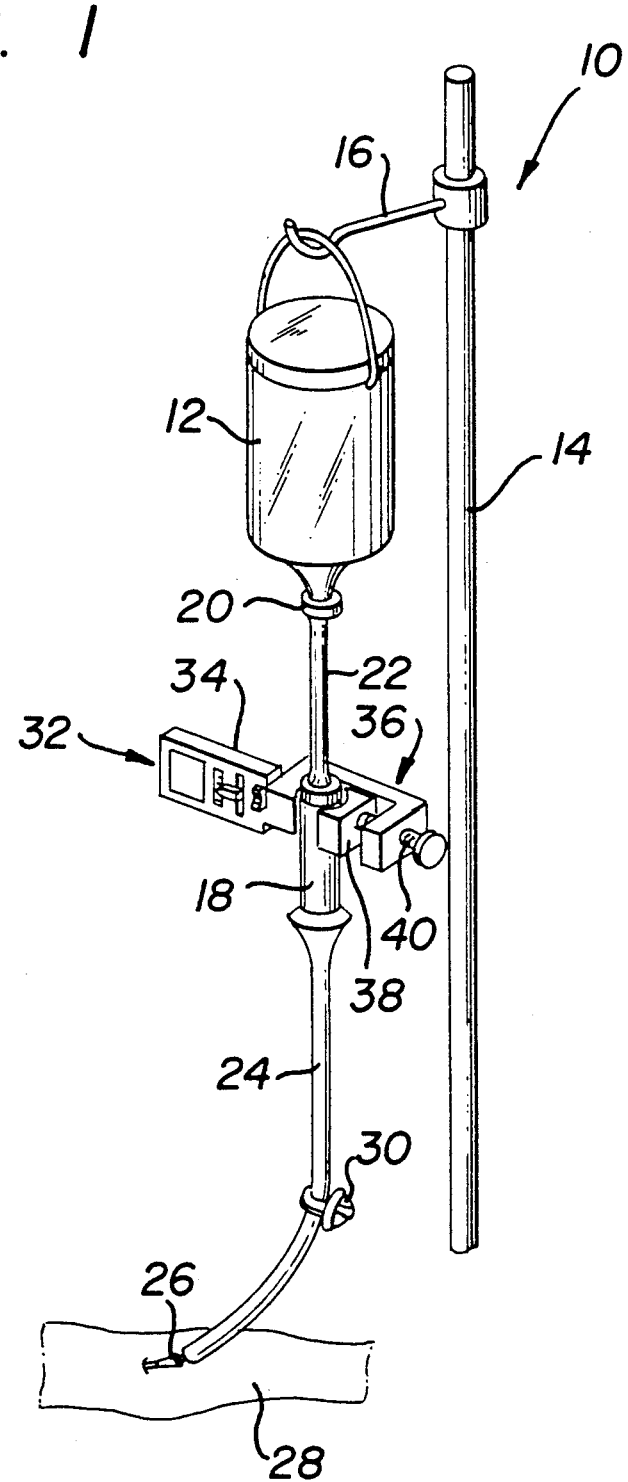
FIG. 1 is a perspective view of an IV set including a portable, self-contained, infusion monitor according to a preferred embodiment of the present invention.
Figure 2:
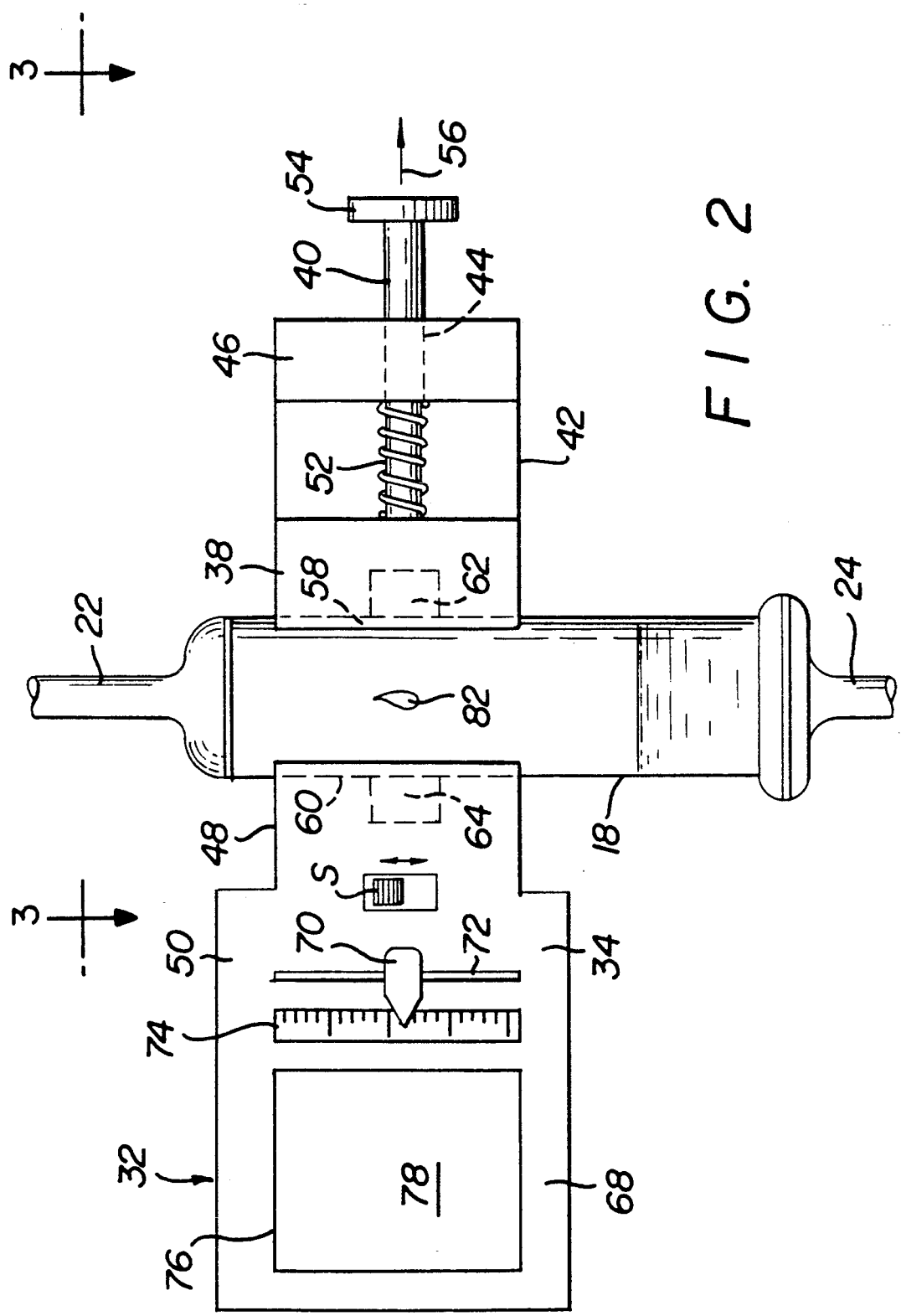
FIG. 2 is a side elevational view of the portable infusion monitor attached to the drip chamber of the IV set.
Figures 3, 5:
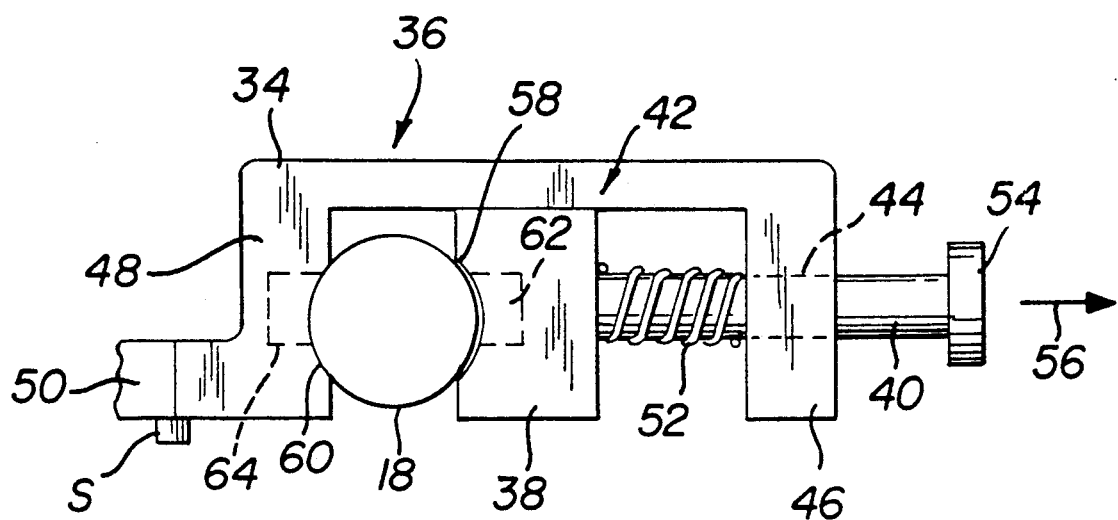
FIG. 3 is a top plan view of a part of the infusion monitor taken along the lines 3—3 in FIG. 2.
FIG. 5 is a table illustrating typical drop factors for tubing used in conventional IV sets.

Referring now to FIGS. 1-3, there is shown a conventional intravenous (IV) set generally indicated at 10 for infusing a liquid containing medicine and/or nutrients to a patient. The IV set includes a bottle 12 containing a supply of the liquid to be infused and a stand or post 14 which carries a hook 16 at its upper end for supporting the bottle 12. A drip chamber 18 is connected to an outlet 20 at the bottom of the bottle 12 via a first length of IV tubing 22. A second length of IV tubing 24 connects the drip chamber 18 to a needle 26 which, as shown, is inserted into the patient's arm 28. A mechanical clamp 30 is affixed to the second length of IV tubing 24 between the drip chamber 18 and the needle 26 for controlling the rate at which the liquid is administered to the patient.

According to the present invention, a portable infusion monitor designated generally at 32 is provided for determining the volumetric flow rate of liquid, e.g., cubic centimeters per hour, flowing through the IV set 10 at a given setting of the adjustable clamp 30. The portable monitor 32 is designed to be quickly and easily attached to the drip chamber 18 and then quickly detached and removed in one piece for us with still another IV set to administer medication and/or nutrients to another patient.

To this end, the portable monitor 32 includes an elongated housing 34 containing all of the major monitor components and an adjustable, biased, clamping means designated generally at 36.

The clamping means 36 includes a movable contact member 38 mounted at one end of an elongated shaft 40. The contact member 38 is adapted to move longitudinally within a generally "U" shaped section 42 of the housing 34. The shaft 40 extends through a hole or bore 44 provided within an end wall 46 which forms one leg of the generally "U" shaped section 42 as best shown in FIG. 3. The other leg of the "U" shaped section 42 is formed by an opposite lateral wall 48 which adjoins the main body 50 of the housing 34.

A coil spring 52 is mounted around the shaft 40 between the contact member 38 and the end wall 46. This coil spring 52 biases the contact member 38 for movement in a direction toward the opposite lateral wall 48.

A circular knob 54 is attached to the outer end of the shaft 40 for pulling the contact member 38 in an opposite direction away from the lateral wall 48 and against the bias spring 52.

To attach the monitor 32 onto the drip chamber 18, the operator grasps the circular knob 54 and pulls the knob away from the end wall 46 in the direction shown by the arrow 56. This opens a space between the contact member 38 and the opposite lateral wall 48.

With the "U" shaped section 42 of the housing 34 held opposite the drip chamber 18, the latter is gently guided into the open space between the contact member 38 and the lateral wall 48 and the knob 54 is then released. Upon release of the knob 54, the compressed coil spring 52 biases the contact member 38 against the side wall of the drip chamber 18 and also forces the drip chamber 18 firmly into contact with the lateral wall 48. Both the contact member 38 and the lateral wall 48 are shaped with an arcuate surface as shown at 58, 60, respectively, in order to firmly grasp and properly locate the drip chamber 18.

The biasing force exerted by the coil spring 52 should be sufficient to lock the monitor 32 firmly in place around the drip chamber 18 in the manner as described hereinabove. However, the spring 52 should not be so strong as to cause damage to the drip chamber 18 which is normally made of relatively weak plastic material.

Mounted inside the contact member 38 is a light source 62 such as a light emitting diode or an infrared light bulb, for example. The light source 62 is adapted to direct a continuous beam of light through the drip chamber 18 in the direction of the opposite lateral wall 48. A photoelectric cell 64 or other light sensing device is mounted within the lateral wall 48 and senses the presence of the light beam emitted from the light source 62. The light source 62 and the photoelectric cell 64 together constitute a drop detector which is generally designated at 66 in the circuit diagram of FIG. 4. Operation of the drop detector will be described in greater detail hereinafter.

The main body 50 of the housing 34 extends outwardly from the adjustable clamping means 36 and carries a front panel 68. The panel 68 includes a main switch S, e.g. a single pole slide switch, and an adjustable control 70 which slides up and down inside an elongated slot 72 and along side a scale 74. The scale 74 is provided with markings indicating appropriate drop factor values (see FIG. 6, for example). Also included within the panel 68 is a rectangular window 76 through which a liquid crystal display (LCD) is exposed as shown at 78.

Figure 4:
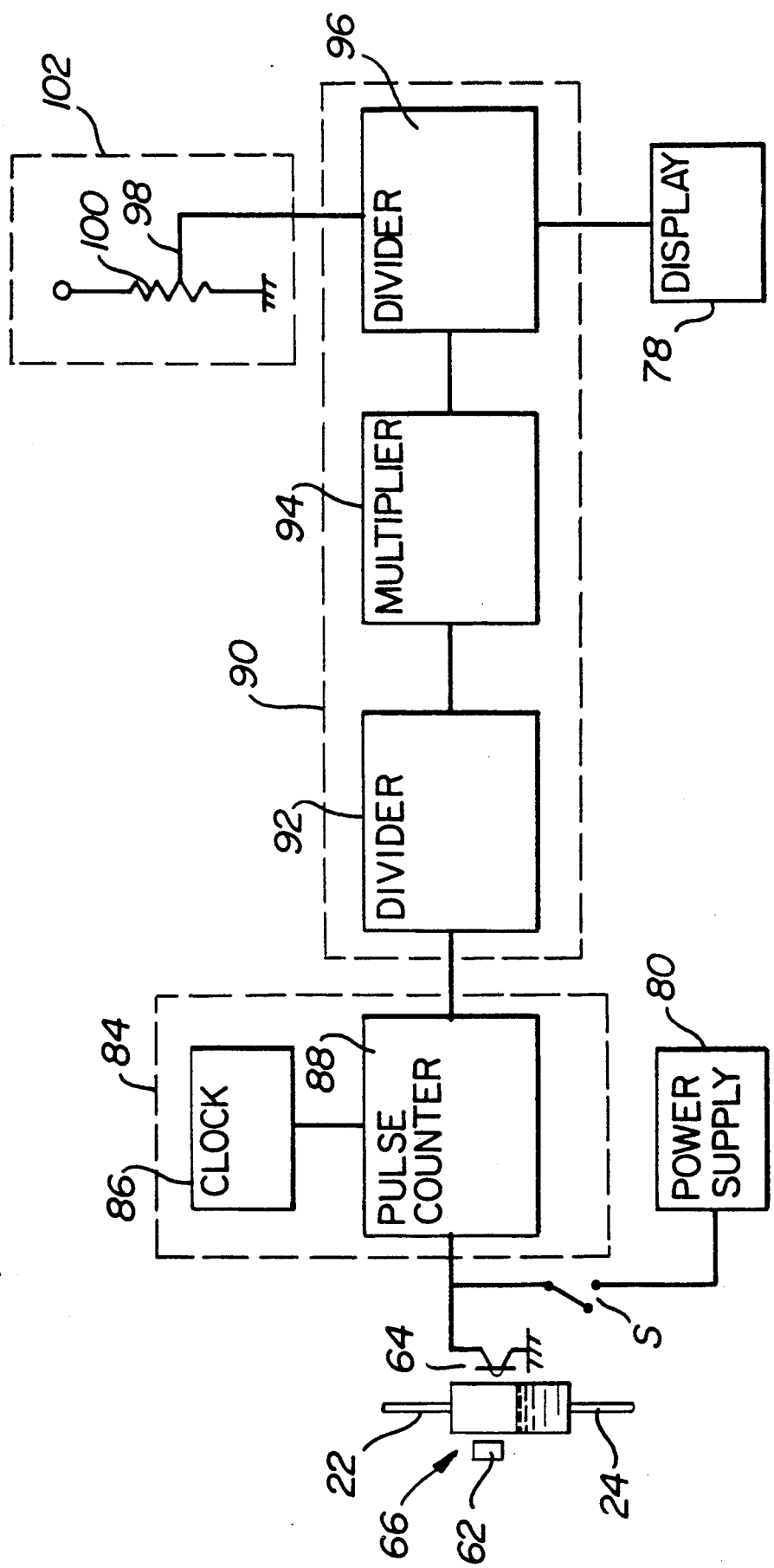
FIG. 4 is a block diagram illustrating the circuit components of the monitor shown in FIGS. 1 and 2.
Figure 7:
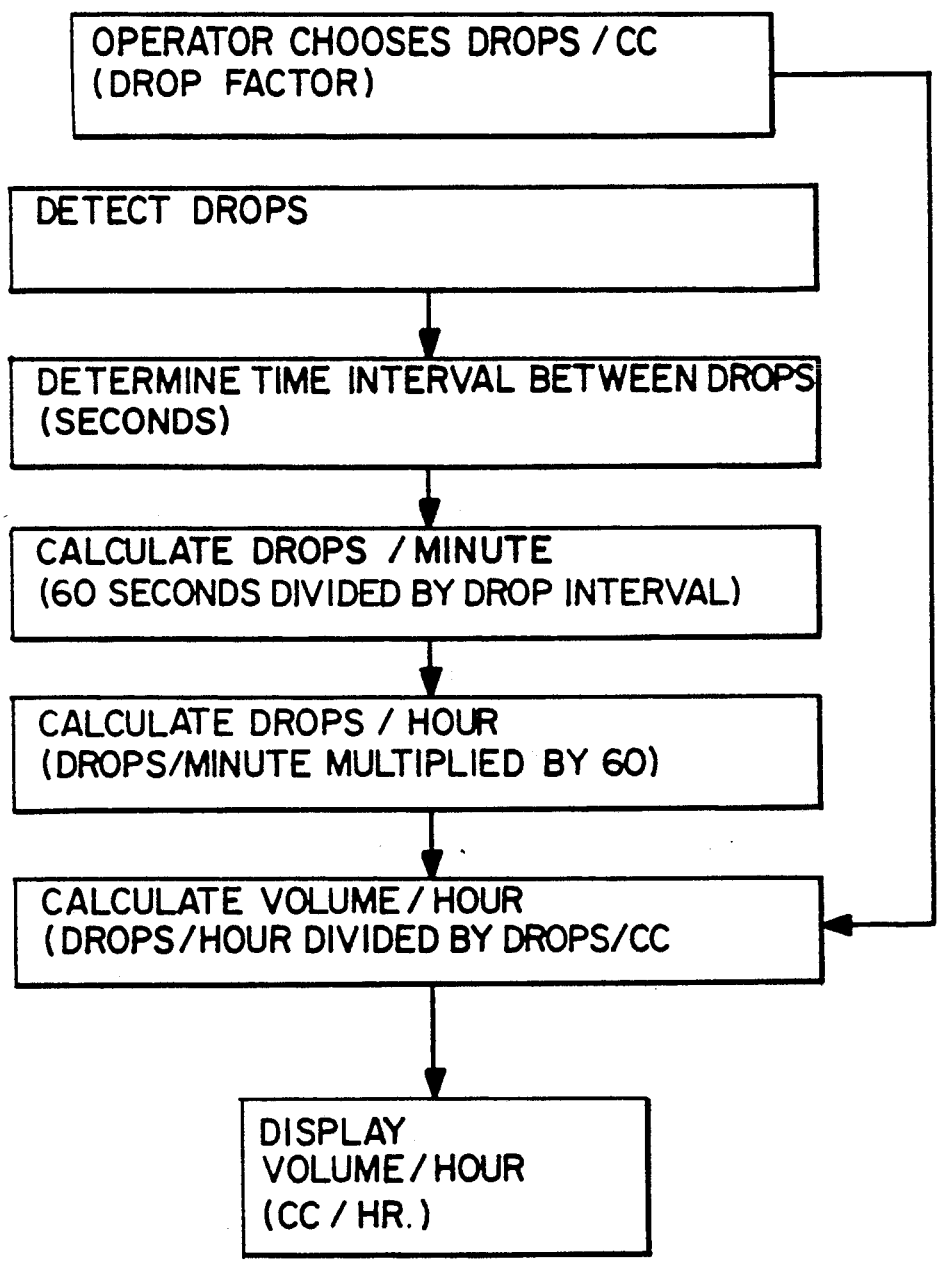
FIG. 7 is a flow chart illustrating operation of the monitor of the invention.

Turning now to the block diagram shown in FIG. 4 and also the flow chart illustrated in FIG. 7, operation of the portable infusion monitor 32 may be explained as follows:

The monitor 32 is activated by closing the switch S which connects the portable power supply 80, e.g. a low voltage D.C. battery, to the monitor circuits and also energizes the drop detector 66. Each drop 82 of liquid which falls through the drip chamber 18 interrupts the beam of light emitted by the light source 62 and produces a signal at the photoelectric cell 64.

This signal is fed to a drop interval counter 84 which includes a clock 86 and a pulse counter 88. The clock 86 produces regularly timed pulses once every second, for example. The pulse counter 88 counts the number of pulses produced by the clock 86 between successive drops of liquid and produces a signal representing the actual time interval between the drops. This signal is then fed to a calculator circuit 90.

The calculator circuit 90 in this embodiment of the monitor includes a first divider 92, a multiplier 94 and a second divider 96. The two dividers 92 and 96 are interconnected by the multiplier 94. The two dividers and the multiplier are well known integrated type circuits that are commonly found today in many standard, electronic digital calculators, for example.

The function of the first divider 92 is to calculate the drop rate, i.e. drops per minute, by dividing the measured drop interval into the number of seconds in one minute, i.e. sixty (60). The multiplier 94 then converts this calculation into "drops per hour" by multiplying the output of the divider 92 by the number minutes in each hour, i.e. sixty (60).

As indicated, the attending physician usually prescribes the intravenous medication in volumetric units, e.g. cubic centimeters per hour (cc's/hr). It is therefore necessary to calculate the volumetric flow rate using the drop rate value produced by the multiplier 94 and also the drop factor of the IV tubing which is expressed as the number of drops per unit of volume, e.g. milliliters (ml).

The operator determines the correct drop factor to be used with a given IV set 10 by examining the markings on the IV tubing package or from any other available source. The monitor 32 is then calibrated by moving the slide control 70 up or down within the slot 72 until it points to the selected drop factor on the scale 74.

Although not shown in the drawing, the slide control 70 is connected to the center tap 98 of a variable potentiometer 100. The potentiometer 100 and the slide control 70 together with the scale 74 constitute an input signal generating means which is designated generally at 102 in FIG. 3.

Thus, when the slide control 70 is adjusted to choose a particular drop factor for the IV set 10 in the manner as described above, the potentiometer 100 is set to produce a corresponding voltage. This voltage serves as an input signal representing the selected drop factor which is fed directly to the second divider 96.

The second divider 96 calculates the volumetric flow rate (e.g. cc's/hr) by dividing the drop rate value produced by the multiplier 94 by the value of the input signal from the potentiometer 100 representing the drop factor.

The output signal from the second divider 96 is the instantaneous volumetric flow rate for the liquid passing through the IV set 10 at the time when each drop falls through the drip chamber 18. This signal may of course vary from one drop to the next during operation of the IV set.

The output signal from the calculator circuit 90 is then fed to the visual display 78. Preferably, as mentioned, the display is a liquid crystal display (LCD) which is mounted on the panel 68 inside the window 76.

During the initial set up of the IV system, the instanteous volumetric flow rate as determined by the monitor 32 of the invention can be visually observed while the operator manually adjusts the clamp 30. This procedure is continued until the monitor indicates that the IV system has reached the prescribed volumetric flow rate and has stabilized at this rate. The monitor may then be removed or it may be left in place for periodic checking by the operator.

The monitor 32 is easily removed by simply pulling the circular knob 54 to release the contact member 38 and allow the drip chamber 18 to be carefully withdrawn from the unit.

In FIG. 5, there is shown a number of typical drop factors for conventional IV tubing. Referring to the table, one milliliter (ml) of liquid flowing through one of the IV tubings indicated will produce 10, 15, 20, etc., drops of liquid in the drip chamber.

This relationship is a function of the size of the IV tubing. As indicated, drop factor values are readily available from a number of different sources, e.g. markings on the tubing, manufacturer's specification, etc.

Figure 6:
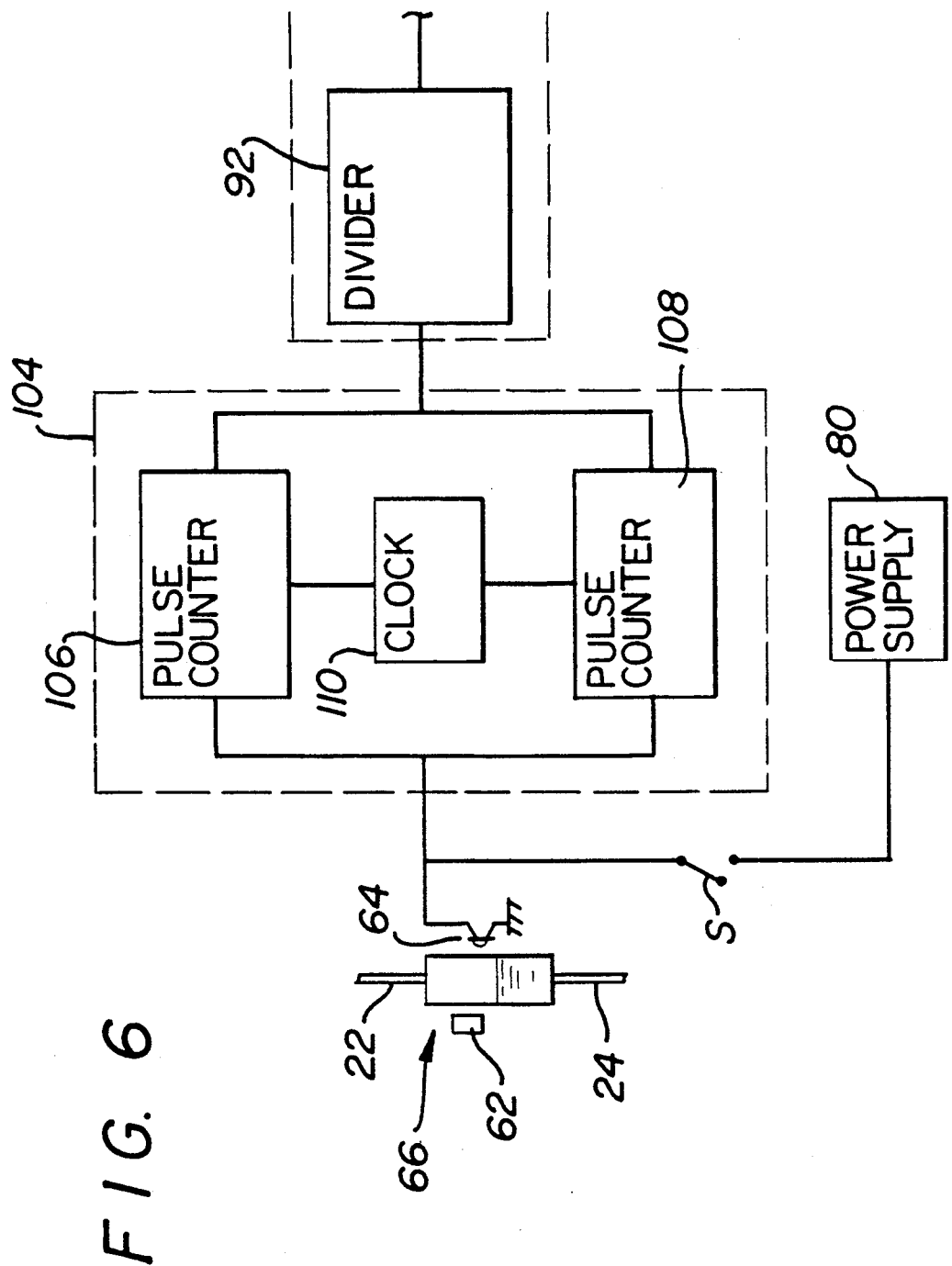
FIG. 6 is a view similar to FIG. 4 illustrating a modification of the circuit components of the monitor.

FIG. 6 shows a modification of the monitor of the invention wherein the drop interval counter 104 includes a pair of pulse counters 106 and 108 and a clock 110 connected to each counter. The counters 106 and 108 are arranged in such manner that each counter is adapted to count the pulses from the clock 110 between alternate drops 82 of liquid. Thus, with the occurance of each drop, one counter 106 begins its count of the pulse interval between that drop and the next succeeding drop while the other counter 108 stops its count of the drop interval begun by the previous drop. This process continues throughout operation of the monitor.

Other modifications of the monitor according to the invention will readily occur to those skilled in the art. For example, it is entirely possible to employ the light source inside the housing and the photoelectric cell inside the movable contact member. Moreover, it is possible to eliminate the multiplier in the calculator circuit and to employ a first divider which can calculate the number of drops per hour directly.

It will be readily seen from the foregoing that the present invention provides a unique portable self-contained infusion monitor which can be easily attached to the drip chamber of a conventional IV set for measuring the volumetric flow rate of an infusion liquid and then quickly detached for use in another IV set without disturbing operation of either system. Moreover, the monitor can be quickly calibrated to accomodate IV sets employing IV tubing having different drop factors and is therefore accurate and very convenient to use. Furthermore, the monitor of the invention is simple in construction and does not require the complex control systems used in prior art devices and is also easy and inexpensive to manufacture.

What is claimed is:

1. A device for monitoring the volumetric flow rate of an infusion liquid flowing through an IV set comprising, in combination:
   a housing;
   means for detachably mounting said housing onto a drip chamber forming part of said IV set;
   means for detecting each drop of liquid falling through said drip chamber;
   a clock in said housing;
   a pulse counter in said housing coupled to said detecting means for counting the number of pulses produced by said clock between successive drops falling through said drip chamber;
   means coupled to said pulse counter for calculating the rate at which each drop falls through said drip chamber and for producing a signal corresponding thereto;
   a variable potentiometer in said housing;
   means external to said housing for manually setting said potentiometer and for generating an input signal representing the drop volume;
   means coupled to said variable potentiometer for combining said input signal and said drop rate signal and for producing an output signal representing the volumetric flow rate of liquid flowing through said IV set; and means for visually displaying said output signal.

2. A device for monitoring the volumetric flow rate of an infusion liquid flowing through an IV set comprising, in combination:
   a housing;
   means for detachably mounting said housing onto a drip chamber forming part of said IV set;
   means for detecting each drop of liquid falling through said drip chamber;
   a clock in said housing;
   a pulse counter in said housing coupled to said detecting means for counting the number of pulses produced by said clock between successive drops falling through said drip chamber;
   a first divider coupled to said pulse counter for calculating the rate at which each drop falls through said drip chamber and for producing a signal corresponding thereto;
   a variable potentiometer in said housing;
   means external to said housing for manually setting said potentiometer and for generating an input signal representing the drop volume;
   a second divider coupled to said input signal generating means for combining said input signal and said drop rate signal and for producing an output signal representing the volumetric flow rate of liquid flowing through said IV set; and means for visually displaying said output signal.

3. A device for monitoring the volumetric flow rate of an infusion liquid flowing through an IV set comprising, in combination:
   a housing;
   means for detachably mounting said housing onto a drip chamber forming part of said IV set;
   a light source for passing a beam of light through said drip chamber;
   a photoelectric cell for detecting drops of liquid which fall through said drip chamber and interrupt said beam of light;
   a clock in said housing;
   a pulse counter in said housing coupled to said photoelectric cell for counting the number of pulses produced by said clock between successive drops falling through said drip chamber;
   a first divider coupled to said pulse counter for calculating the rate at which each drop falls through said chamber and for producing a signal corresponding thereto;
   a variable potentiometer;
   means external to said housing for manually setting said potentiometer and producing an input signal representing the drop volume;
   a second divider coupled to said variable potentiometer for combining said input signal and said drop rate signal and for producing an output signal representing the volumetric flow rate of liquid flowing through said IV set; and
   means for visually displaying said output signal.

4. A monitor according to claim 3, wherein said housing includes a surface portion adapted to contact one side of said drip chamber.

5. A monitor according to claim 4, wherein said detachable mounting means includes a movable member and a biasing member for urging said movable member into contact with an opposite side of said drip chamber.

6. A monitor according to claim 5, wherein said photoelectric cell is mounted within said surface portion of said housing and said light source is mounted within said movable member.

7. A monitor according to claim 5, wherein said photoelectric cell is mounted within said movable member and said light source is mounted within said surface portion of said housing.

8. A monitor according to claim 3, further including a multiplier having an input connected to said first divider for converting said drop rate to a higher order of time.

9. A monitor according to claim 3, further including a second pulse counter connected in parallel with said first pulse counter and in series with said photoelectric cell, each of said counters being operative to count the number of pulses produced by said clock between alternate drops of liquid.

10. A device for monitoring the volumetric flow rate of an infusion liquid flowing through an IV set comprising, in combination:
   a housing having a surface portion adapted to contact one side of a drip chamber forming part of said IV set;
   a movable member mounted within said housing;
   biasing means for urging said movable member into contact with an opposite side of said drip chamber;
   a light source mounted in said member for passing a beam of light through said drip chamber;
   a photoelectric cell mounted in said surface portion of said housing for detecting drops of liquid which fall through said drip chamber and interrupt said light beam;
   a clock in said housing;
   a pulse counter in said housing coupled to said photoelectric cell for counting the number of pulses produced by said clock between successive drops falling through said drip chamber;
   a first divider coupled to said pulse counter for calculating the rate at which each drop falls through said chamber and for producing a signal corresponding thereto;
   a variable potentiometer;

means external to said housing for manually setting said potentiometer and producing an input signal representing the drop volume;

a multiplier connected to said first divider for converting said drop rate to a higher; order of time;

a second divider having a first input connected to said multiplier and a second input connected to said potentiometer for operatively converting said drop rate to volumetric flow rate of liquid flowing through said IV set; and means for visually displaying said output signal.

11. A monitor according to claim 10 wherein the means for manually setting said potentiometer comprises a slide control which is movable within a slot in said housing and a scale positioned along side said slot, said scale containing markings corresponding to different values of drop volume.

12. In an IV set including a container for storing an infusion liquid, a drip chamber, a first tube connecting said storage container and said drip chamber and a second tube connecting said drip chamber to an insertion device for introducing said liquid into a human subject, said first tube having a drop factor characterized in that said first tube produces a predetermined number of drops per unit volume when connected to said drip chamber; the combination therewith of a monitor for determining the volumetric flow of liquid passing through said IV set, said monitor comprising, in combination:

a housing;

means for detachably mounting said housing onto said drip chamber;

a light source for passing a beam of light through said drip chamber;

a photoelectric cell for detecting drops of liquid which fall through said drip chamber and interrupt said beam of light;

a clock in said housing;

a pulse counter in said housing coupled to said photoelectric cell for counting the number of pulses produced by said clock between successive drops falling through said drip chamber;

a first divider coupled to said pulse counter for calculating the rate at which each drop falls through said chamber and for producing a signal corresponding thereto;

a variable potentiometer;

a slide control connected to said potentiometer, said slide control being movable within a slot in said housing;

a scale positioned along side said slot, said scale containing markings corresponding to different values of said drop factor whereby said potentiometer may be manually set to produce an input signal representing said drop factor;

a second divider coupled to said variable potentiometer for combining said input signal and said drop rate signal and for producing an output signal representing the volumetric flow rate of liquid flowing through said IV set; and means for visually displaying said output signal.

* * * * *